United States Patent
Wang et al.

(10) Patent No.: US 11,756,191 B2
(45) Date of Patent: Sep. 12, 2023

(54) METHOD AND APPARATUS FOR MAGNETIC RESONANCE IMAGING AND PLAQUE RECOGNITION

(71) Applicant: SHENZHEN INSTITUTES OF ADVANCED TECHNOLOGY, Shenzhen (CN)

(72) Inventors: Shanshan Wang, Shenzhen (CN); Taohui Xiao, Shenzhen (CN); Hairong Zheng, Shenzhen (CN); Xin Liu, Shenzhen (CN); Dong Liang, Shenzhen (CN)

( * ) Notice: Subject to any disclaimer, the term of this patent is extended or adjusted under 35 U.S.C. 154(b) by 616 days.

(21) Appl. No.: 16/979,535

(22) PCT Filed: Dec. 13, 2018

(86) PCT No.: PCT/CN2018/120878
§ 371 (c)(1),
(2) Date: Sep. 10, 2020

(87) PCT Pub. No.: WO2020/118615
PCT Pub. Date: Jun. 18, 2020

(65) Prior Publication Data
US 2020/0410675 A1 Dec. 31, 2020

(51) Int. Cl.
*G06T 7/00* (2017.01)
*A61B 5/00* (2006.01)
(Continued)

(52) U.S. Cl.
CPC ............ *G06T 7/0012* (2013.01); *A61B 5/004* (2013.01); *A61B 5/055* (2013.01); *A61B 5/7257* (2013.01);
(Continued)

(58) Field of Classification Search
None
See application file for complete search history.

(56) References Cited

U.S. PATENT DOCUMENTS

| | | | |
|---|---|---|---|
| 2007/0249931 A1 | 10/2007 | Fain et al. | |
| 2021/0361167 A1* | 11/2021 | Wolfe | ............... A61B 5/7246 |
| 2021/0374950 A1* | 12/2021 | Gao | ................... G06T 7/0012 |

FOREIGN PATENT DOCUMENTS

| CN | 102509113 A | | 6/2012 |
|---|---|---|---|
| CN | 103646410 A | * | 3/2014 |

(Continued)

*Primary Examiner* — Dov Popovici

(57) ABSTRACT

A method for magnetic resonance imaging and plaque recognition includes: obtaining magnetic resonance undersampled K-space data; transforming the magnetic resonance undersampled K-space data to an image domain through inverse Fourier transform to obtain a preprocessed image; reconstructing the preprocessed image through a pre-established deep learning reconstruction model to obtain a high-resolution imaging image of a blood vessel wall; and recognizing plaques in the high-resolution imaging image of the blood vessel wall through a pre-established deep learning plaque recognition model. A neural network corresponding to the pre-established deep learning reconstruction model is a dense connection network. The magnetic resonance undersampled K-space data is head-and-neck combined magnetic resonance undersampled K-space data of the blood vessel wall.

16 Claims, 5 Drawing Sheets

(51) Int. Cl.
    *A61B 5/055*     (2006.01)
    *G06T 11/00*     (2006.01)
    *A61B 5/02*      (2006.01)

(52) U.S. Cl.
    CPC .......... *A61B 5/7267* (2013.01); *G06T 11/005* (2013.01); *A61B 5/02007* (2013.01); *A61B 2576/02* (2013.01); *G06T 2207/10064* (2013.01); *G06T 2207/20081* (2013.01); *G06T 2207/20084* (2013.01); *G06T 2207/30101* (2013.01); *G06T 2210/36* (2013.01); *G06T 2210/41* (2013.01)

(56)         References Cited

FOREIGN PATENT DOCUMENTS

| | | | | |
|---|---|---|---|---|
| CN | 103646410 | A | | 3/2014 |
| CN | 106056647 | A | | 10/2016 |
| CN | 106530258 | A | | 3/2017 |
| CN | 107064845 | A | | 8/2017 |
| CN | 108542390 | A * | 9/2018 | ............. A61B 5/055 |
| CN | 108542390 | A | | 9/2018 |
| EP | 3392832 | A1 | | 10/2018 |

* cited by examiner

METHOD AND APPARATUS FOR MAGNETIC RESONANCE IMAGING AND PLAQUE RECOGNITION

CROSS-REFERENCE TO THE RELATED APPLICATIONS

This application is the national stage entry of International Application No. PCT/CN2018/120878, filed on Dec. 13, 2018, the entire contents of which are incorporated herein by reference.

TECHNICAL FIELD

The present application belongs to the field of an image processing technology, and in particular relates to a method and an apparatus for magnetic resonance imaging and plaque recognition.

BACKGROUND

Magnetic resonance imaging is a relatively advanced modern medical imaging technology, and has great significance in scientific research and clinical diagnosis. However, a slow speed of the magnetic resonance imaging seriously hinders the development of the magnetic resonance imaging technology. Magnetic resonance blood vessel wall imaging is a non-invasive imaging means that can detect head-and-neck integrated arterial blood vessel walls and plaques. The imaging speed and quality thereof will affect a recognition effect of the head-and-neck plaques.

Current magnetic resonance imaging technologies generally achieve head-and-neck integrated imaging of a blood vessel wall just from the perspective of physical methods for adjusting imaging. It is difficult to achieve a high spatial resolution and short scanning time by these methods. Therefore, the plaque recognition in the head-and-neck integrated imaging of the blood vessel wall is more difficult.

At present, there is no effective solution for performing efficient imaging and recognition of head-and-neck plaques through the magnetic resonance imaging technology.

SUMMARY OF THE INVENTION

The object of the present application is to provide a method and an apparatus for magnetic resonance imaging and plaque recognition, which can transform an undersampled image into a high-resolution image, and can accurately recognize positions of the plaques from the high-resolution image.

The method and apparatus for magnetic resonance imaging and plaque recognition according to the present application are implemented as follows:

A method for magnetic resonance imaging and plaque recognition includes steps of:
  obtaining magnetic resonance undersampled K-space data;
  transforming the magnetic resonance undersampled K-space data to an image domain to obtain a preprocessed image;
  reconstructing the preprocessed image through a pre-established deep learning reconstruction model to obtain a high-resolution imaging image of a blood vessel wall, and
  recognizing plaques in the high-resolution imaging image of the blood vessel wall through a pre-established deep learning plaque recognition model.

In one embodiment, transforming the magnetic resonance undersampled K-space data to an image domain to obtain a preprocessed image includes:
  transforming the magnetic resonance undersampled K-space data to the image domain through inverse Fourier transform to obtain the preprocessed image.

In one embodiment, a neural network corresponding to the pre-established deep learning reconstruction model is a dense connection network, and the neural network corresponding to the pre-established deep learning reconstruction model sequentially includes:
  a first convolutional layer, a first dense connection block, a first conversion layer, a second dense connection block, a second conversion layer, a third dense connection block, a third conversion layer, a fourth dense connection block, a fourth conversion layer, a fifth dense connection block, a fifth conversion layer, and a second convolutional layer, wherein each dense connection block includes multiple dense connection layers, and the features of each layer in each dense connection block are input to all subsequent layers, so that the features of all layers are connected in series.

In one embodiment, the deep learning reconstruction model is established as follows:
  obtaining a predesigned deep learning reconstruction model;
  training the predesigned deep learning reconstruction model according to a sample and a label which are obtained in advance; and
  using the trained model as the pre-established deep learning reconstruction model;
  wherein the sample is an undersampled image of the blood vessel wall, and the label is a fully-sampled image of the blood vessel wall corresponding to the undersampled image of the blood vessel wall.

In one embodiment, a neural network corresponding to the pre-established deep learning plaque recognition model sequentially includes:
  multiple convolutional layers, a pooling layer, a first residual block, multiple convolutional layers, a second residual block, multiple convolutional layers, a third residual block, multiple convolutional layers, a pooling layer, multiple convolutional layers, a pooling layer, and multiple full-connection layers.

In one embodiment, the deep learning plaque recognition model is established as follows: obtaining a predesigned deep learning plaque recognition model; training the predesigned deep learning plaque recognition model according to a sample and a label which are obtained in advance; and using the trained model as the pre-established deep learning plaque recognition model; wherein the sample is a fully-sampled image of the blood vessel wall, and the label is coordinate information of the plaques.

In one embodiment, the magnetic resonance undersampled K-space data is head-and-neck combined magnetic resonance undersampled K-space data of the blood vessel wall.

An apparatus for magnetic resonance imaging and plaque recognition includes:
  an obtaining module configured to obtain magnetic resonance undersampled K-space data;
  a transformation module configured to transform the magnetic resonance undersampled K-space data to an image domain to obtain a preprocessed image;
  a reconstruction module configured to reconstruct the preprocessed image through a pre-established deep learning reconstruction model to obtain a high-resolution imaging image of a blood vessel wall; and a recognition module configured to recognize plaques in the high-resolution imaging image of the blood vessel wall through a pre-established deep learning plaque recognition model.

In one embodiment, the transformation module is specifically configured to transform the magnetic resonance undersampled K-space data to the image domain through inverse Fourier transform to obtain the preprocessed image.

In one embodiment, a neural network corresponding to the pre-established deep learning reconstruction model is a dense connection network, and the neural network corresponding to the pre-established deep learning reconstruction model sequentially includes:

a first convolutional layer, a first dense connection block, a first conversion layer, a second dense connection block, a second conversion layer, a third dense connection block, a third conversion layer, a fourth dense connection block, a fourth conversion layer, a fifth dense connection block, a fifth conversion layer, and a second convolutional layer, wherein each dense connection block includes multiple dense connection layers, and the features of each layer in each dense connection block are input to all subsequent layers, so that the features of all layers are connected in series.

In one embodiment, the above apparatus further includes:

a first establishment module configured to establish the deep learning reconstruction model as follows:

obtaining a predesigned deep learning reconstruction model;

training the predesigned deep learning reconstruction model according to a sample and a label which are obtained in advance; and using the trained model as the pre-established deep learning reconstruction model;

wherein the sample is an undersampled image of the blood vessel wall, and the label is a fully-sampled image of the blood vessel wall corresponding to the undersampled image of the blood vessel wall.

In one embodiment, a neural network corresponding to the pre-established deep learning plaque recognition model sequentially includes:

multiple convolutional layers, a pooling layer, a first residual block, multiple convolutional layers, a second residual block, multiple convolutional layers, a third residual block, multiple convolutional layers, a pooling layer, multiple convolutional layers, a pooling layer, and multiple full-connection layers.

In one embodiment, the above apparatus further includes a second establishment module configured to establish the deep learning plaque recognition model as follows: obtaining a predesigned deep learning plaque recognition model; training the predesigned deep learning plaque recognition model according to a sample and a label which are obtained in advance; and using the trained model as the pre-established deep learning plaque recognition model; wherein the sample is a fully-sampled image of the blood vessel wall, and the label is coordinate information of the plaques.

In one embodiment, the magnetic resonance undersampled K-space data is head-and-neck combined magnetic resonance undersampled K-space data of the blood vessel wall.

A terminal device includes a processor and a memory for storing executable instructions of the processor, wherein when the processor executes the instructions, the following steps are implemented:

obtaining magnetic resonance undersampled K-space data;

transforming the magnetic resonance undersampled K-space data to an image domain to obtain a preprocessed image;

reconstructing the preprocessed image through a pre-established deep learning reconstruction model to obtain a high-resolution imaging image of a blood vessel wall, and recognizing plaques in the high-resolution imaging image of the blood vessel wall through a pre-established deep learning plaque recognition model.

A computer-readable storage medium stores computer instructions thereon, wherein when the instructions are executed, the following steps are implemented:

obtaining magnetic resonance undersampled K-space data;

transforming the magnetic resonance undersampled K-space data to an image domain to obtain a preprocessed image;

reconstructing the preprocessed image through a pre-established deep learning reconstruction model to obtain a high-resolution imaging image of a blood vessel wall; and recognizing plaques in the high-resolution imaging image of the blood vessel wall through a pre-established deep learning plaque recognition model.

According to the method and apparatus for magnetic resonance imaging and plaque recognition provided in the present application, the preprocessed image is obtained by transforming the magnetic resonance undersampled K-space data to the image domain; then based on the deep learning reconstruction model, the preprocessed image is reconstructed to obtain a high-resolution imaging image of the blood vessel wall; and then by the deep learning plaque recognition model, the plaques in the high-resolution imaging image of the blood vessel wall are recognized. That is, only by obtaining the magnetic resonance undersampled K-space data, the plaque condition can be finally determined. Due to the above solution, the existing technical problem that the plaque condition cannot be easily and efficiently determined is solved, and the technical effects of simply and efficiently transforming the undersampled image into a high-resolution image and accurately recognizing the plaque condition from the high-resolution image are achieved.

BRIEF DESCRIPTION OF THE DRAWINGS

To describe the technical solutions in the embodiments of the present application or the prior art more clearly, the following briefly introduces the accompanying drawings required for describing the embodiments or the prior art. Apparently, the accompanying drawings in the following description show merely some embodiments of the present application, and a person of ordinary skill in the art may still derive other drawings from these accompanying drawings without creative efforts.

DETAILED DESCRIPTION

In order to enable those skilled in the art to better understand the technical solutions in the present application, the following will clearly and completely describe the technical solutions in the embodiments of the present application with reference to the drawings in the embodiments of the present application. Obviously, the described embodiments are only a part rather than all of the embodiments of the present application. Based on the embodiments in the present application, all other embodiments obtained by those of ordinary skill in the art without creative efforts should fall within the protection scope of the present application.

In view of the existing problems in the high-definition imaging and accurate recognition of head-and-neck plaques, how to reconstruct the undersampled image with a high resolution in conjunction with deep neural networks is considered in the present embodiment, and then the plaques are recognized by the deep neural networks based on a high-resolution image. Therefore, the scanning time can be effectively shortened and the accuracy rate of plaque recognition can be improved.

Figure 1:
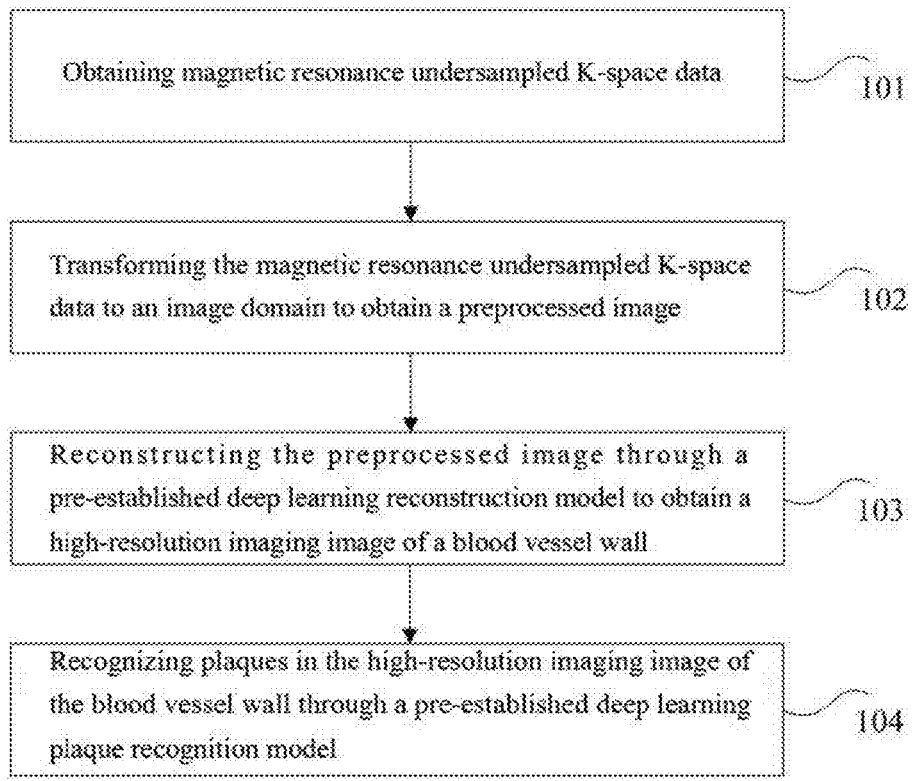
FIG. 1 is a flowchart of a method for magnetic resonance imaging and plaque recognition according to an embodiment of the present application.

FIG. 1 is a flowchart of a method for magnetic resonance imaging and plaque recognition method according an embodiment of the present application. Although the present application provides method operation steps or an apparatus structure as shown in the following embodiments or drawings, more or less operation steps or module units may be included in the method or apparatus based on conventional or non-creative labor. In the steps or structure where there is no necessary causal relationship logically, the execution order of these steps or the module structure of the apparatus is not limited to the execution order or module structure described in the embodiments and shown in the drawings of the present application. When applied to an actual apparatus or terminal product, the described method or module structure may be executed sequentially or in parallel according to the method or module structure connection shown in the embodiments or drawings (for example, in a parallel-processor or multi-threaded processing environment, even in a distributed processing environment).

Specifically, as shown in FIG. 1, a method for magnetic resonance imaging and plaque recognition according to an embodiment of the present application may include:

In step 101: magnetic resonance undersampled K-space data is obtained.

The K-space is the dual space of an ordinary space under Fourier transform. The K-space is mainly used in the imaging analysis of magnetic resonance imaging. The concept of the K-space is also used in the radio frequency waveform design in the magnetic resonance imaging, the initial state preparation in quantum computing and other fields, wherein K corresponds to the number of waves appearing in wave mathematics. All the above maybe considered as a concept of "frequency-space-frequency".

The undersampled K-space data may be obtained by magnetic resonance scanning. The K-space data is not a real image that can be distinguished by human eyes. Therefore, in actual use, it is necessary to transform the K-space data to an image domain, that is, the real image that can be intuitively identified by humans.

An under sampling means maybe used for scanning in order to shorten the scanning time when the magnetic resonance scanning is performed. An under sampling ratio during the specific scanning may be selected according to actual needs, which is not limited in the present application.

In step 102: a preprocessed image is obtained by transforming the magnetic resonance undersampled K-space data to the image domain.

The actual transformation from the undersampled K-space data to the image domain may be performed through inverse Fourier transform, and the preprocessed image is obtained by transforming the magnetic resonance undersampled K-space data to the image domain. Since the K-space is the dual space of an ordinary space under Fourier transform, the data can be transformed to the ordinary space through the inverse Fourier transform, that is, to obtain an image identifiable by humans.

In step 103: the preprocessed image is reconstructed through a pre-established deep learning reconstruction model to obtain a high-resolution imaging image of the blood vessel wall.

In the above step 102 to step 103, the preprocessed image is obtained by transforming the K-space data to the image domain. However, since the initial K-space data is undersampled, the above preprocessed image is also undersampled, i.e, a low-resolution image. It is generally difficult to obtain an ideal recognition effect for the plaques based on such a low-resolution image.

To this end, the preprocessed image transformed to the image domain may be reconstructed to obtain a high-resolution imaging image of the blood vessel wall. Specifically, the above preprocessed image may be reconstructed through the pre-established deep learning reconstruction model. A neural network corresponding to the pre-established deep learning reconstruction model may be a dense connection network, and the neural network corresponding to the pre-established deep learning reconstruction model may sequentially include: a first convolutional layer, a first dense connection block, a first conversion layer, a second dense connection block, a second conversion layer, a third dense connection block, a third conversion layer, a fourth dense connection block, a fourth conversion layer, a fifth dense connection block, a fifth conversion layer and a second convolutional layer. Each dense connection block includes multiple dense connection layers, and the features of each layer in each dense connection block are input to all subsequent layers, so that the features of all layers are connected in series.

That is, the neural network corresponding to the pre-established deep learning reconstruction model may include: 2 convolutional layers, 5 dense connection blocks, and 5 conversion layers. Therefore, due to the dense connection blocks, the propagation of the features can be enhanced, the multiplexing of the features is supported, and the number of parameters is reduced, so that the pre-established deep learning reconstruction model can have a better reconstruction capability.

In step 104: the plaques in the high-resolution imaging image of the blood vessel wall are recognized through a pre-established deep learning plaque recognition model.

By the image reconstruction operation in step 103, a high-resolution imaging image of the blood vessel wall can be obtained, and plaque recognition may be performed on the image to obtain more accurate plaque information, such as specific positions, sizes and shapes of the plaques.

When plaque recognition is performed, the recognition may be performed through the pre-established deep learning plaque recognition model. A neural network corresponding to the plaque recognition model may sequentially include: multiple convolutional layers, a pooling layer, a first residual block, multiple convolutional layers, a second residual block, multiple convolutional layers, a third residual block, multiple convolutional layers, a pooling layer, multiple convolutional layers, a pooling layer and multiple full-connection layers.

For example, the neural network corresponding to the plaque recognition model may include: 12 convolutional layers, 3 residual blocks, 3 pooling layers, and 3 full-connection layers.

However, it should be noted that the hierarchical structure in the neural network listed in the present embodiment is only an exemplary description, and the specific number of each layer may be selected according to actual needs, which is not limited in the present application.

In the above embodiment, the preprocessed image is obtained by transforming the magnetic resonance undersampled K-space data to the image domain; then based on the deep learning reconstruction model, the preprocessed image is reconstructed to obtain a high-resolution imaging image of the blood vessel wall; and then by the deep learning plaque recognition model, the plaques in the high-resolution imaging image of the blood vessel wall are recognized. That is, only by obtaining the magnetic resonance undersampled K-space data, the plaque condition can be finally determined. Due to the above solution, the existing technical problem that the plaque condition cannot be easily and efficiently determined is solved, and the technical effects of simply and efficiently transforming the undersampled image into a high-resolution image and accurately recognizing the plaque condition from the high-resolution image are achieved.

The above deep learning reconstruction model may be established as follows:

S1: obtaining a predesigned deep learning reconstruction model;

S2: training the predesigned deep learning reconstruction model according to a sample and a label which are obtained in advance; and S3: using the trained model as the pre-established deep learning reconstruction model.

The sample is an undersampled image of the blood vessel wall, and the label is a fully-sampled image of the blood vessel wall corresponding to the undersampled image of the blood vessel wall.

The above magnetic resonance undersampled K-space data may be, but not limited to, the head-and-neck combined magnetic resonance undersampled K-space data of the blood vessel wall.

The above method is described below in conjunction with a specific embodiment. However, it should be noted that the specific embodiment is only for better illustrating the application and does not constitute an improper limitation of the present application.

In the present embodiment, a deep learning algorithm is configured to perform fast high-resolution reconstruction on a magnetic resonance image of the blood vessel wall, and to automatically detect and classify head-and-neck plaques.

That is, an artificial intelligence integrated method for imaging of the blood vessel wall and automatic detection of the plaques is provided. Specifically, the method may include; data collection, sample making, construction of a deep convolutional reconstruction network and a detection network, network training and testing, and real-time imaging and plaque detection.

Figure 2:
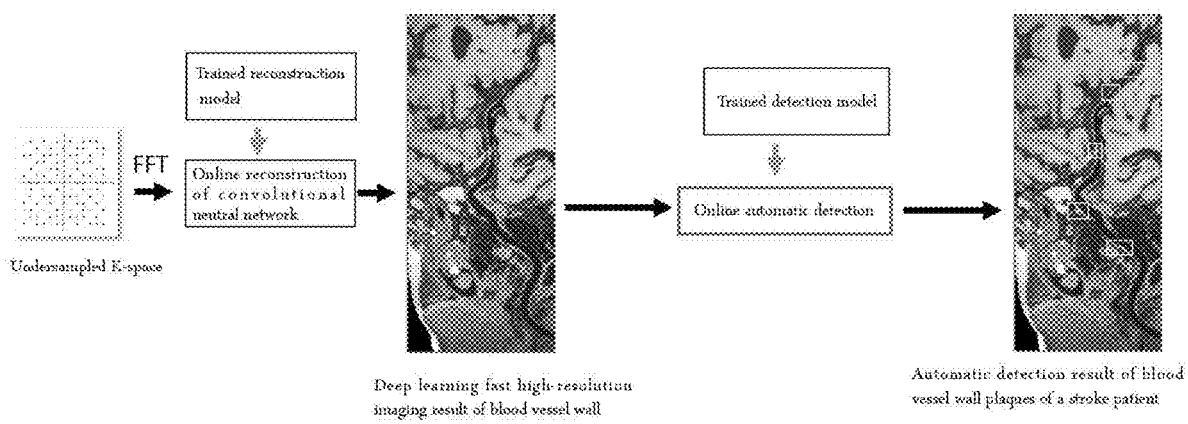
FIG. 2 is a data flow diagram of integrated head-and-neck magnetic resonance imaging and detection of a blood vessel wall according to the present application.

As shown in FIG. 2, the obtained magnetic resonance undersampled k-space data is subjected to inverse Fourier transform (FFT) to obtain an image domain thereof, and then the well-trained deep learning reconstruction model is used for online reconstruction to obtain the reconstructed magnetic resonance image of the blood vessel wall. Then, the reconstructed magnetic resonance image of the blood vessel wall are subjected to online automatic detection, and the plaques of the head-and-neck blood vessel wall can be automatically recognized through the deep learning detection model.

Further, the data used in the present embodiment may be the head-and-neck magnetic resonance image of the blood vessel wall collected on a retrospective magnetic resonance scanner. The data of the plaques may be marked by professionals. In actual implementation, after being uniformly preprocessed, the collected data is made into input and output samples of the deep learning network, so as to train the reconstruction and detection deep neural network models.

Figure 3:
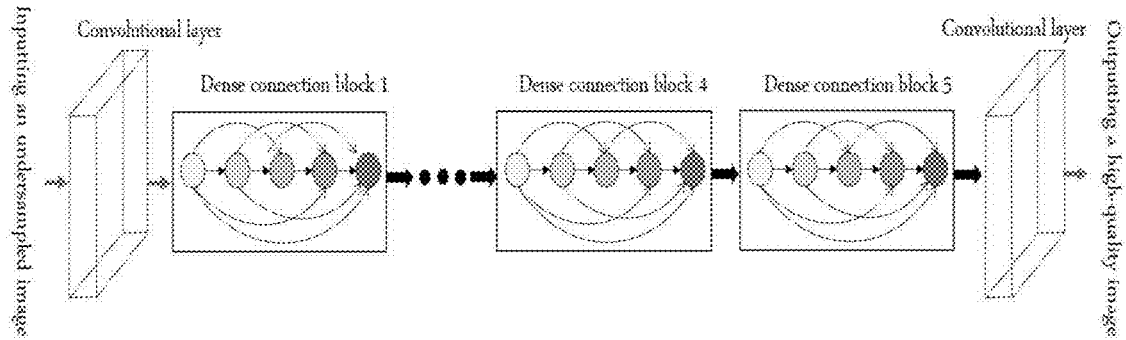
FIG. 3 is a schematic diagram of a deep convolutional reconstruction network of a blood vessel wall image according to the present application.

During image reconstruction, a dense connection network (DenseNet) may be used. The used reconstruction network may be as shown in FIG. 3. The network may include: 2 convolutional layers, 5 dense blocks and 5 transition layers. The dense connection blocks input the features of each layer to all subsequent layers, so that the features of all layers may be connected in series, thereby achieving the advantages of enhancing feature propagation, supporting feature multiplexing, and reducing the number of parameters. In the present embodiment, the dense connection of 5 layers exists in the dense connection blocks, and the conversion layer is connected after each dense connection block. The conversion layer consists of batch normalization, convolution, and average pooling. The input of the reconstruction network is an undersampled image of the blood vessel wall, and the output label corresponds to the fully-sampled image of the blood vessel wall.

Figure 4:
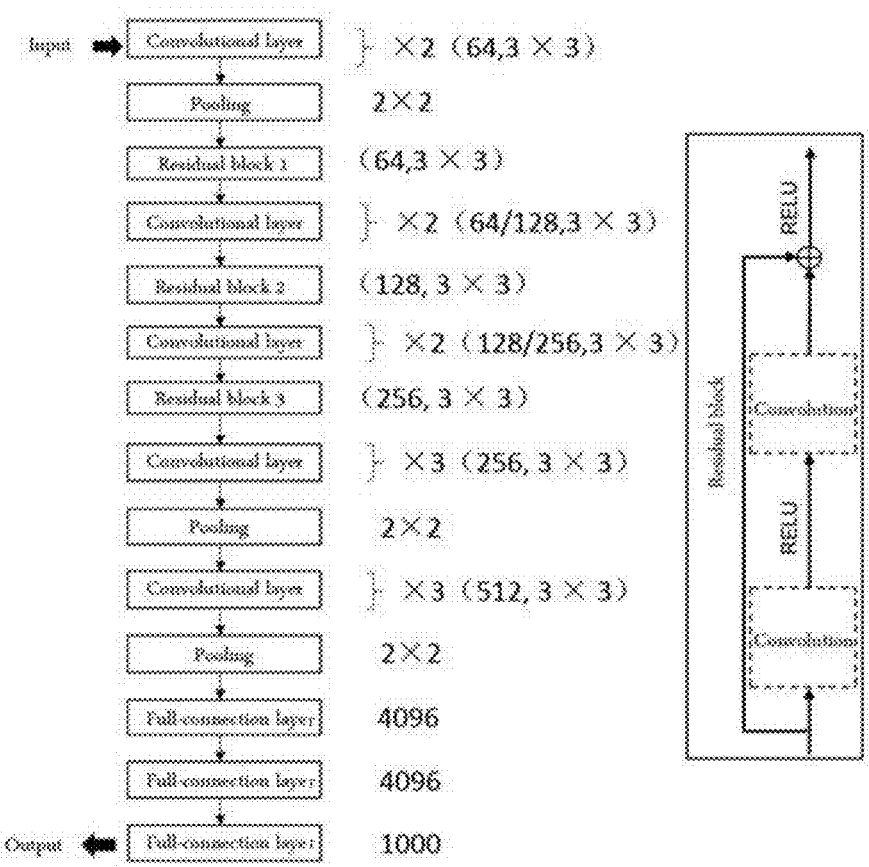
FIG. 4 is a schematic diagram of a deep convolutional detection network of head-and-neck plaques according to the present application.

In the present embodiment, the residual blocks are introduced into the deep neural network. A structure of the neural network may include 12 convolutional layers, 3 residual blocks, 3 pooling layers, and 3 full-connection layers as shown in FIG. 4. In FIG. 4, the ×2 or ×3 on the edge of the convolutional layer means consecutive 2 or 3 convolutional layers, and the values in brackets (64/128, 3×3) mean that the numbers of feature maps set in the consecutive 2 convolutional layers are 64 and 128 respectively, and that the size of a convolutional kernel is 3×3. The pooling operation adopts the maximum pooling. For the three full-connection layers, the number of neurons in each layer may be configured to: 4096, 4096 and 1000 respectively, and finally the output of a detection result may be obtained through softmax. After the residual blocks are introduced, the deep neural network can better extract the basic features such as target points and edges, and is favorable to improve detection performances for the plaques. The input of the detection network for head-and-neck plaques is a fully-sampled image of the blood vessel wall, and the output label is coordinate information of the corresponding marked plaques.

Figure 5:
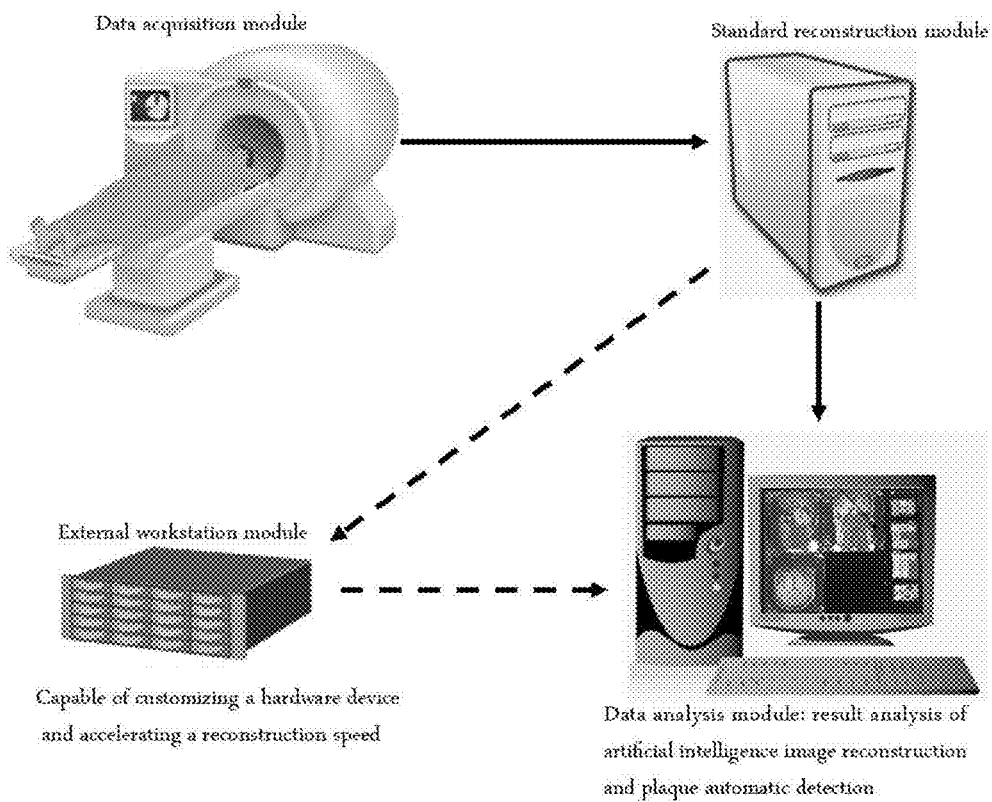
FIG. 5 is a schematic diagram of an integrated imaging and recognition apparatus according to the present application.

In the present embodiment, there is provided an integrated application apparatus for artificial intelligence imaging and diagnosis. As shown in FIG. 5, the apparatus may include: a data acquisition module, a standard reconstruction module, an external workstation module, and a data analysis module:

1) The data acquisition module is configured to directly perform highly undersampled scanning on the head and neck of a human body to obtain magnetic resonance K-space data of the blood vessel wall;
2) The standard reconstruction module is configured to reconstruct original K-space data and reconstruct the same into an image domain image that can be analyzed by human vision;

Specifically, the above K-space data may be processed through inverse Fourier transform, so as to obtain an image domain image that can be analyzed by human vision.

3) The external workstation module is configured to assist the standard reconstruction module to shorten the reconstruction time. The output of the standard reconstruction module or the external workstation module will be input to the data analysis module;

The external workstation module may be understood as an auxiliary module of the above standard reconstruction module. For example, if a processing load of the standard reconstruction module is relatively high, then a part of the processing tasks may be assigned to the external workstation module and processed through the assistance of the external workstation module. During specific processing, the external workstation module may operate in parallel with the standard reconstruction module, thereby shortening the reconstruction time.

4) The data analysis module is configured to perform fast high-resolution reconstruction on the image domain image reconstructed by the standard reconstruction module or the external workstation module, and automatically recognize the reconstructed high-resolution image by using a deep learning detection network that has been implanted in the module, thereby detecting head-and-neck plaques.

For the standard reconstruction module, only the image domain image that can be analyzed by human vision is obtained, but the image is still an undersampled image with a low resolution. The effect of performing plaque recognition based on such an image is not very good. Therefore, the high-resolution reconstruction may be performed on the undersampled image through the deep neural network in the data analysis module, that is, a high-resolution image is obtained, and plaque recognition may be further performed based on the obtained high-resolution image.

In the above embodiment, a deep convolutional reconstruction network for fast high-resolution imaging and a deep convolutional detection network for automatic recognition and diagnosis of the head-and-neck plaques are provided. The artificial intelligence imaging and recognition method based on deep learning can be applied to the magnetic resonance imaging of the blood vessel wall and plaque detection.

Figure 6:
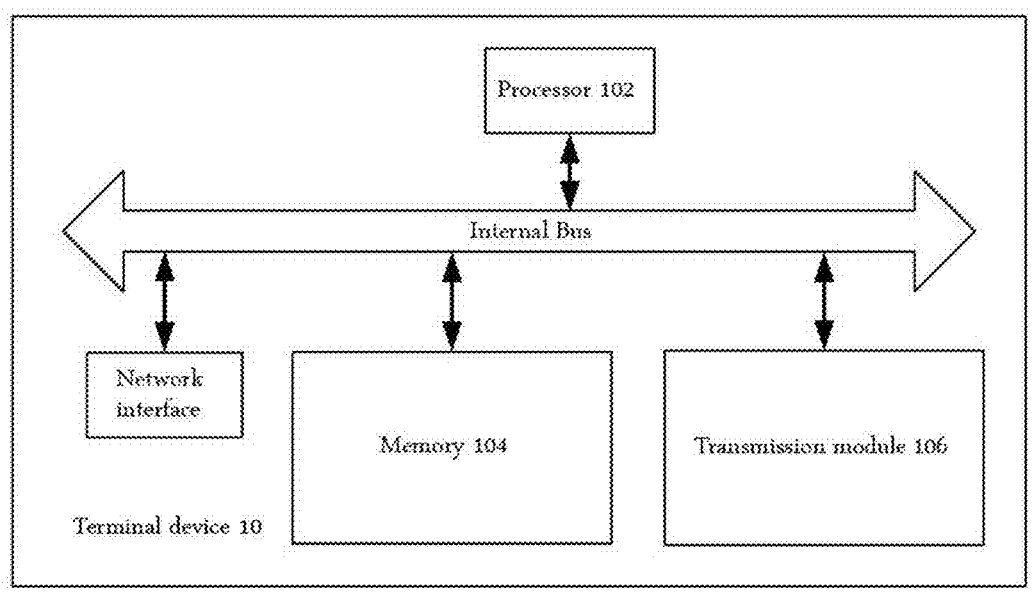
FIG. 6 is a schematic diagram of the architecture of a terminal device according to the present application.

The method embodiment provided in the above embodiment of the present application may be executed in a terminal device, a computer terminal, or a similar computing apparatus. By taking operation on the terminal device as an example, FIG. 6 is a hardware structure block diagram of a computer terminal for a method for magnetic resonance imaging and plaque recognition according to an embodiment of the present invention. As shown in FIG. 6, the terminal device 10 may include one or more (only one is shown in the drawing) processors 102 (the processor 102 may include, but not limited to, a processing apparatus such as a microprocessor MCU or a programmable logic device FPGA), a memory 104 for storing data, and a transmission module 106 for communication functions. Those of ordinary skill in the art can understand that the structure shown in FIG. 6 is only schematic, and does not limit the structure of the above electronic apparatus. For example, the terminal device 10 may also include more or fewer components than those shown in FIG. 6, or have a different configuration from that shown in FIG. 6.

The memory 104 may be configured to store software programs of application software and modules, for example the program instructions/modules corresponding to the method for magnetic resonance imaging and plaque recognition in the embodiment of the present invention. The processor 102 runs the software programs and modules stored in the memory 104, so as to perform various functional applications and data processing, that is, to achieve the above method for magnetic resonance imaging and plaque recognition. The memory 104 may include a high-speed random access memory, and may also include a non-volatile memory, such as one or more magnetic storage devices, a flash memory, or other non-volatile solid-state memories. In some examples, the memory 104 may further include memories remotely disposed with respect to the processor 102, and these remote memories may be connected to the computer terminal 10 via a network. Examples of the above network include, but not limited to, the Internet, a corporate intranet, a local area network, a mobile communication network, and combinations thereof.

The transmission module 106 is configured to receive or send data via the network. The specific examples of the above network may include a wireless network provided by a communication provider of the computer terminal 10. In one example, the transmission module 106 includes a network interface controller (NIC), which may be connected to other network devices through a base station so as to communicate with the Internet. In one example, the transmission module 106 may be a radio frequency (RF) module, which is configured to communicate with the Internet in a wireless manner.

Figure 7:
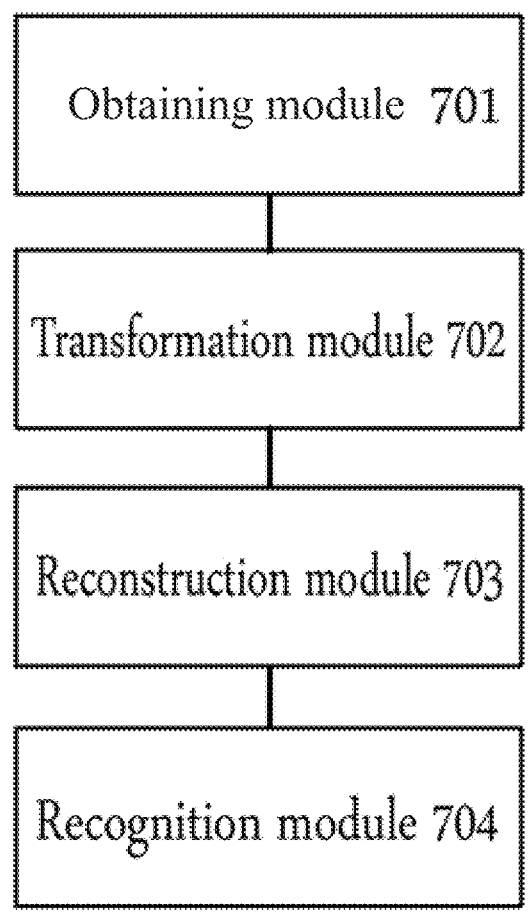
FIG. 7 is a structural block diagram of an apparatus for magnetic resonance imaging and plaque recognition according to the present application.

At the software level, the above apparatus for magnetic resonance imaging and plaque recognition may be as shown in FIG. 7 and includes:

an obtaining module 701 configured to obtain magnetic resonance undersampled K-space data;

a transformation module 702 configured to transform the magnetic resonance undersampled K-space data to an image domain to obtain a preprocessed image;

a reconstruction module 703 configured to reconstruct the preprocessed image through a pre-established deep learning reconstruction model to obtain a high-resolution imaging image of the blood vessel wall; and a recognition module 704 configured to recognize plaques in the high-resolution imaging image of the blood vessel wall through a pre-established deep learning plaque recognition model.

In one embodiment, the transformation module 702 may be specifically configured to transform the magnetic resonance undersampled K-space data to the image domain through inverse Fourier transform to obtain a preprocessed image.

In one embodiment, a neural network corresponding to the pre-established deep learning reconstruction model is a dense connection network, and the neural network corresponding to the pre-established deep learning reconstruction model may sequentially include: a first convolutional layer, a first dense connection block, a conversion layer, a second dense connection block, a second conversion layer, a third dense connection block, a third conversion layer, a fourth dense connection block, a fourth conversion layer, a fifth dense connection block, a fifth conversion layer and a second convolutional layer, wherein each dense connection block includes multiple dense connection layers, and the features of each layer in each dense connection block are input to all subsequent layers, so that the features of all layers are connected in series.

In one embodiment, the above apparatus for magnetic resonance imaging and plaque recognition may further include: a first establishment module configured to establish the deep learning reconstruction model in the following manner: obtaining a predesigned deep learning reconstruction model; training the predesigned deep learning reconstruction model according to a sample and a label which are obtained in advance; and using the trained model as the pre-established deep learning reconstruction model; wherein the sample is an undersampled image of the blood vessel wall, and the label is a fully-sampled image of the blood vessel wall corresponding to the undersampled image of the blood vessel wall.

In one embodiment, the neural network corresponding to the above pre-established deep learning plaque recognition model may sequentially include: multiple convolutional layers, a pooling layer, a first residual block, multiple convolutional layers, a second residual block, multiple convolutional layers, a third residual block, multiple convolutional layers, a pooling layer, multiple convolutional layers, a pooling layer and multiple full-connection layers.

In one embodiment, the above apparatus for magnetic resonance imaging and plaque recognition may further include: a second establishment module configured to establish the deep learning plaque recognition model in the following manner: obtaining a predesigned deep learning plaque recognition model; training the predesigned deep learning plaque recognition model according to a sample and a label which are obtained in advance; and using the trained model as the pre-established deep learning plaque recognition model; wherein the sample is a fully-sampled image of the blood vessel wall, and the label is coordinate information of the plaques.

In one embodiment, the above magnetic resonance undersampled K-space data may be head-and-neck combined magnetic resonance undersampled K-space data of the blood vessel wall.

An embodiment of the present application also provides a specific implementation manner of an electronic device that can implement all the steps of the method for magnetic resonance imaging and plaque recognition in the foregoing embodiments, and the electronic device specifically includes the following content:

a processor, a memory, a communication interface and a bus.

The processor, the memory, and the communication interface communicate with one another via the bus 4. The processor is configured to call a computer program in the memory, and the processor implements all steps of the head-and-neck combined imaging method based on deep prior learning in the above embodiments when executing the computer program. For example, the following steps are implemented when the processor executes the computer program:

Step 1: obtaining magnetic resonance undersampled K-space data;

Step 2: transforming the magnetic resonance undersampled K-space data to an image domain to obtain a preprocessed image;

Step 3: reconstructing the preprocessed image through a pre-established deep learning reconstruction model to obtain a high-resolution imaging image of a blood vessel wall; and Step 4: recognizing plaques in the high-resolution imaging image of the blood vessel wall through a pre-established deep learning plaque recognition model.

It can be seen from the above description that the preprocessed image is obtained by transforming the magnetic resonance undersampled K-space data to the image domain; then based on the deep learning reconstruction model, the preprocessed image is reconstructed to obtain a high-resolution imaging image of the blood vessel wall; and then by the deep learning plaque recognition model, the plaques in the high-resolution imaging image of the blood vessel wall are recognized. That is, only by obtaining the magnetic resonance undersampled K-space data, the plaque condition can be finally determined. Due to the above solution, the existing technical problem that the plaque condition cannot be easily and efficiently determined is solved, and the technical effects of simply and efficiently transforming the undersampled image into a high-resolution image and accurately recognizing the plaque condition from the high-resolution image are achieved.

An embodiment of the present application also provides a computer-readable storage medium capable of implementing all the steps of the method for magnetic resonance imaging and plaque recognition in the above embodiments. The computer-readable storage medium stores a computer program thereon. When the computer program is executed by the processor, all steps of the method for magnetic resonance imaging and plaque recognition in the above embodiments are implemented. For example, when the processor executes the computer program, the following steps are implemented:

Step 1: obtaining magnetic resonance undersampled K-space data;

Step 2: transforming the magnetic resonance undersampled K-space data to an image domain to obtain a preprocessed image;

Step 3: reconstructing the preprocessed image through a pre-established deep learning reconstruction model to obtain a high-resolution imaging image of a blood vessel wall; and Step 4: recognizing plaques in the high-resolution imaging image of the blood vessel wall through a pre-established deep learning plaque recognition model.

It can be seen from the above description that the preprocessed image is obtained by transforming the magnetic resonance undersampled K-space data to the image domain; then based on the deep learning reconstruction model, the preprocessed image is reconstructed to obtain a high-resolution imaging image of the blood vessel wall; and then by the deep learning plaque recognition model, the plaques in the high-resolution imaging image of the blood vessel wall are recognized. That is, only by obtaining the magnetic resonance undersampled K-space data, the plaque condition can be finally determined. Due to the above solution, the existing technical problem that the plaque condition cannot be easily and efficiently determined is solved, and the technical effects of simply and efficiently transforming the undersampled image into a high-resolution image and accurately recognizing the plaque condition from the high-resolution image are achieved.

The various embodiments in the description are described in a progressive manner, the same or similar parts between the various embodiments may be referred to each other, and each embodiment focuses on the differences from the other embodiments. In particular, for the hardware and system embodiments, since it is basically similar to the method embodiment, the description is relatively simple, and the relevant parts may be referred to the description of the method embodiment.

The foregoing describes specific embodiments of the description. Other embodiments are within the scope of the appended claims. In some cases, the actions or steps described in the claims may be executed in a different order than that in the embodiments and still achieve desired results. In addition, the processes described in the drawings can achieve the desired results without necessarily requiring the shown specific order or sequential order. In some embodiments, multitasking and parallel processing are also possible or may be advantageous.

Although providing the method operation steps as described in the embodiments or flowcharts, the present application may include more or fewer operation steps based on conventional or uninventive labor. The sequence of the steps listed in the embodiments is only one of the execution orders of the steps, and does not represent the only execution order. When executed in an actual apparatus or client product, the steps may be executed sequentially or in parallel according to the method shown in the embodiments or the drawings (for example, a parallel processor or multi-threaded processing environment).

The system, apparatus, modules or units illustrated in the above embodiments may be specifically implemented by computer chips or entities, or by products with certain functions. A typical implementation apparatus is a computer. Specifically, the computer may be, for example, a personal computer, a laptop computer, a vehicle-mounted human-computer interaction device, a cellular phone, a camera phone, a smart phone, a personal digital assistant, a media player, a navigation device, an email device, a game console, a tablet computer, a wearable device, or any combination of these devices.

Although providing the method operation steps as described in the embodiments or flowcharts, the embodiments of the description may include more or fewer operation steps based on conventional or uninventive means. The sequence of the steps listed in the embodiments is only one of the execution orders of the steps, and does not represent the only execution order. When executed in an actual apparatus or terminal product, the steps may be implemented sequentially or in parallel according to the methods shown in the embodiments or drawings (for example, a parallel processor or multi-threaded processing environment, or even a distributed data processing environment). The terms "include", "contain", or any other variants are intended to cover the nonexclusive containing, such that the processes, methods, products or devices including a series of elements not only include those elements, but also include other unclearly listed elements, or also include the inherent elements of such processes, methods, products or devices. Without more limitations, the existence of other same or equivalent elements in the process, method, product, or device that including such element is not excluded.

For the convenience of description, the above apparatus is divided into various modules by function for description. Of course, the functions of the various modules may be implemented in the same one or more software and/or hardware during implementation of the embodiments of the present invention, and the modules that implement the same function may also be implemented by a combination of multiple sub-modules or sub-units. The apparatus embodiments described above are merely schematic. For example, the partitioning of the units may be a logical functional partitioning. There may be other partitioning modes during actual implementation. For example, multiple units or components may be combined or integrated into another system, or some features may be ignored or not executed. In addition, mutual coupling or direct coupling or communication connection that is shown or discussed may be indirect coupling or communication connection of the apparatuses or units through some interfaces, and may be in electrical, mechanical or other forms.

Those skilled in the art also know that, in addition to implementing the controller in a purely computer-readable program code manner, it is totally implementable to logically program the method steps, so that the controller achieves the same functions in the form of a logic gate, a switch, a specific integrated circuits, a programmable logic controller, an embedded microcontroller and the like. Therefore, the controller may be regarded as a hardware component, and the apparatuses included in the controller for realizing various functions may also be regarded as a structure within the hardware component. Or even, the apparatus for realizing various functions may be regarded as both a software module for realizing the method and a structure within the hardware component.

The present invention is described with reference to the flowcharts and/or block diagrams of the method, the device (system) and the computer program product according to the embodiments of the present invention. It should be understood that each process and/or block in the flowcharts and/or block diagrams, and combinations of processes and/or blocks in the flowcharts and/or block diagrams may be realized by computer program instructions. These computer program instructions may be provided to a generate-purpose computer, a special-purpose computer, an embedded processor, or processors of other programmable data processing devices, so as to create a machine, such that an apparatus for realizing functions designated in one or more processes in the flowcharts and/or in one or more blocks in the block diagrams may be created by instructions executed by a computer or processors of other programmable data processing devices.

These computer program instructions may further be stored in a computer readable memory that can boot a computer or other programmable data processing devices to work in a specific way, such that a manufactured product containing an instruction apparatus may be created by the instructions stored in the computer readable memory, and the instruction apparatus realizes the functions designated in one or more processes in the flowcharts and/or in one or more blocks in the block diagrams.

These computer program instructions may further be loaded into a computer or other programmable data processing devices, such that a series of operating steps may be executed on the computer or other programmable data processing devices, so as to generate processes realized by the computer, such that steps for realizing the functions designated in one or more processes in the flowcharts and/or in one or more blocks in the block diagrams may be provided by the instructions executed on the computer or other programmable data processing devices.

In a typical configuration, a computing device includes one or more processors (CPUs), input/output interfaces, network interfaces, and memories.

The memory may include a computer readable medium in the form of a non-persistent memory, a random access memory (RAM), and/or a non-volatile memory, such as a read only memory (ROM) or a flash random access memory (flash RAM). The memory is an example of the computer readable medium.

The computer readable medium includes both persistent and non-persistent and removable and non-removable media that may be implemented in any method or technology for storage of information. The information may be computer readable instructions, data structures, program modules or other data. Examples of the computer storage medium includes, but not limited to, a phase-change RAM (PRAM), a static random access memory (SRAM), a dynamic random access memory (DRAM), other types of random access memories (RAM), a read only memory (ROM), an electrically erasable programmable read only memory (EEPROM), a flash memory or other memory technologies, a compact disk read only memory (CD-ROM), a digital versatile disk (DVD) or other optical storages, magnetic cassettes, magnetic tapes, magnetic disk storages or other magnetic storage devices, or any other non-transmission mediums that can be used to store information for access by a computing device. As defined herein, the computer readable medium does not include transitory computer readable media, such as modulated data signals and carrier waves.

It should be appreciated by those skilled in the art that, the embodiments of the description may be provided as methods, systems or computer program products. Therefore, complete hardware embodiments, complete software embodiments or the hardware and software combined embodiments may be adopted in the embodiments of the description. In addition, the embodiments of the description may adopt one or more computer program products that may be implemented by computer-usable storage mediums (include but not limited to a disk storage, a CD-ROM, an optical storage, etc.) including computer-usable program codes.

The embodiments of the description may be described in the general context of computer executable instructions executed by a computer, for example, program modules. Generally, the program modules include routines, programs, objects, components, data structures, etc., that perform specific tasks or implement specific abstract data types. The embodiments of the description may also be practiced in distributed computing environments. In these distributed computing environments, remote processing devices connected through a communication network perform the tasks. In the distributed computing environments, the program modules may be located in local and remote computer storage mediums including storage devices.

The various embodiments in the description are described in a progressive manner, the same or similar parts between the various embodiments may be referred to each other, and each embodiment focuses on the differences from the other embodiments. In particular, for the system embodiment, since it is basically similar to the method embodiment, the description is relatively simple, and the relevant parts may be referred to the description of the method embodiment. In the description of the present invention, the description of referring terms such as "an embodiment", "some embodiments", "an example", "a specific example" or "some examples" means that particular features, structures, materials or characteristics described in combination with the embodiments or examples are included in at least one embodiment or example of the embodiments of the description. In the description, schematic description of the above terms does not necessarily refer to the same embodiment or example. Furthermore, the described particular features, structures, materials or characteristics can be integrated with any one or more embodiments or examples in a proper manner. In addition, those skilled in the art can integrate or combine various embodiments or examples described in the description, as well as features of various embodiments or examples without contradicting each other.

The foregoing is only the preferred embodiments of the embodiments of the description, and is not intended to limit the embodiments of the description. Various changes and modifications may be made to the embodiments of the description for those skilled in the art. Any modifications, equivalent substitutions, improvements, etc., made within the spirit and principles of the embodiments of the description should be included within the scope of the appended claims of the embodiments of the description.

What is claimed is:

1. A method for magnetic resonance imaging and plaque recognition, comprising steps of:
    obtaining magnetic resonance undersampled K-space data;
    transforming the magnetic resonance undersampled K-space data to an image domain to obtain a preprocessed image,
    reconstructing the preprocessed image through a pre-established deep learning reconstruction model to obtain a high-resolution imaging image of a blood vessel wall; and
    recognizing plaques in the high-resolution imaging image of the blood vessel wall through a pre-established deep learning plaque recognition model.

2. The method according to claim 1, wherein the step of transforming the magnetic resonance undersampled K-space data to the image domain to obtain the preprocessed image comprises:
    transforming the magnetic resonance undersampled K-space data to the image domain through inverse Fourier transform to obtain the preprocessed image.

3. The method according to claim 1, wherein a neural network corresponding to the pre-established deep learning reconstruction model is a dense connection network, and the neural network corresponding to the pre-established deep learning reconstruction model sequentially comprises:
    a first convolutional layer, a first dense connection block, a first conversion layer, a second dense connection block, a second conversion layer, a third dense connection block, a third conversion layer, a fourth dense connection block, a fourth conversion layer, a fifth dense connection block, a fifth conversion layer, and a second convolutional layer, wherein each dense connection block comprises multiple dense connection layers, and features of each layer in each dense connection block are input to all subsequent layers to connect features of the all subsequent layers in series.

4. The method according to claim 1, wherein the pre-established deep learning reconstruction model is established as follows:
    obtaining a predesigned deep learning reconstruction model;
    training the predesigned deep learning reconstruction model according to a sample and a label to obtain a trained model, wherein the sample and the label are obtained in advance; and
    using the trained model as the pre-established deep learning reconstruction model;

wherein the sample is an undersampled image of the blood vessel wall, and the label is a fully-sampled image of the blood vessel wall corresponding to the undersampled image of the blood vessel wall.

5. The method according to claim 1, wherein a neural network corresponding to the pre-established deep learning plaque recognition model sequentially comprises:
multiple convolutional layers, a pooling layer, a first residual block, multiple convolutional layers, a second residual block, multiple convolutional layers, a third residual block, multiple convolutional layers, a pooling layer, multiple convolutional layers, a pooling layer, and multiple full-connection layers.

6. The method according to claim 1, wherein the pre-established deep learning plaque recognition model is established as follows:
obtaining a predesigned deep learning plaque recognition model;
training the predesigned deep learning plaque recognition model according to a sample and a label to obtain a trained model, wherein the sample and the label are obtained in advance; and
using the trained model as the pre-established deep learning plaque recognition model, wherein the sample is a fully-sampled image of the blood vessel wall, and the label is coordinate information of the plaques.

7. The method according to claim 1, wherein the magnetic resonance undersampled K-space data is head-and-neck combined magnetic resonance undersampled K-space data of the blood vessel wall.

8. An apparatus for magnetic resonance imaging and plaque recognition, comprising:
an obtaining module configured to obtain magnetic resonance undersampled K-space data;
a transformation module configured to transform the magnetic resonance undersampled K-space data to an image domain to obtain a preprocessed image;
a reconstruction module configured to reconstruct the preprocessed image through a pre-established deep learning reconstruction model to obtain a high-resolution imaging image of a blood vessel wall; and
a recognition module configured to recognize plaques in the high-resolution imaging image of the blood vessel wall through a pre-established deep learning plaque recognition model.

9. The apparatus according to claim 8, wherein the transformation module is specifically configured to transform the magnetic resonance undersampled K-space data to the image domain through inverse Fourier transform to obtain the preprocessed image.

10. The apparatus according to claim 8, wherein a neural network corresponding to the pre-established deep learning reconstruction model is a dense connection network, and the neural network corresponding to the pre-established deep learning reconstruction model sequentially comprises:
a first convolutional layer, a first dense connection block, a first conversion layer, a second dense connection block, a second conversion layer, a third dense connection block, a third conversion layer, a fourth dense connection block, a fourth conversion layer, a fifth dense connection block, a fifth conversion layer, and a second convolutional layer, wherein each dense connection block comprises multiple dense connection layers, and features of each layer in each dense connection block are input to all subsequent layers to connect features of the all subsequent layers in series.

11. The apparatus according to claim 8, further comprising:
a first establishment module configured to establish the pre-established deep learning reconstruction model as follows:
obtaining a predesigned deep learning reconstruction model;
training the predesigned deep learning reconstruction model according to a sample and a label to obtain a trained model, wherein the sample and the label are obtained in advance; and
using the trained model as the pre-established deep learning reconstruction model;
wherein the sample is an undersampled image of the blood vessel wall, and the label is a fully-sampled image of the blood vessel wall corresponding to the undersampled image of the blood vessel wall.

12. The apparatus according to claim 8, wherein a neural network corresponding to the pre-established deep learning plaque recognition model sequentially comprises:
multiple convolutional layers, a pooling layer, a first residual block, multiple convolutional layers, a second residual block, multiple convolutional layers, a third residual block, multiple convolutional layers, a pooling layer, multiple convolutional layers, a pooling layer, and multiple full-connection layers.

13. The apparatus according to claim 8, further comprising:
a second establishment module configured to establish the ore-established deep learning plaque recognition model as follows:
obtaining a predesigned deep learning plaque recognition model;
training the predesigned deep learning plaque recognition model according to a sample and a label to obtain a trained model, wherein the sample and the label are obtained in advance; and
using the trained model as the pre-established deep learning plaque recognition model;
wherein the sample is a fully-sampled image of the blood vessel wall, and the label is coordinate information of the plaques.

14. The apparatus according to claim 8, wherein the magnetic resonance undersampled K-space data is head-and-neck combined magnetic resonance undersampled K-space data of the blood vessel wall.

15. A terminal device, comprising a processor and a memory for storing executable instructions of the processor, wherein when the processor executes the instructions, the steps of the method according to claim 1 are implemented.

16. A non-transitory computer-readable storage medium storing computer instructions thereon, wherein when the instructions are executed, the steps of the method according to claim 1 are implemented.

* * * * *